United States Patent [19]

Curtze et al.

[11] Patent Number: 5,189,035

[45] Date of Patent: Feb. 23, 1993

[54] FUNGICIDAL FURANONE DERIVATIVES

[75] Inventors: Jürgen Curtze, Johannisberg; Guido Albert, Hackenheim, both of Fed. Rep. of Germany

[73] Assignee: Shell Research Limited, United Kingdom

[21] Appl. No.: 862,080

[22] Filed: Apr. 2, 1992

[30] Foreign Application Priority Data

Apr. 16, 1991 [EP] European Pat. Off. ............ 91106003

[51] Int. Cl.$^5$ ..................... A01N 43/08; A01N 43/84; C07D 295/182; C07D 307/68

[52] U.S. Cl. ............................. 514/231.2; 514/235.5; 514/471; 544/131; 544/146; 544/152; 549/321

[58] Field of Search ....................... 544/131, 146, 152; 549/321; 514/231.2, 235.5, 471

[56] References Cited

FOREIGN PATENT DOCUMENTS 2032058 6/1970 Fed. Rep. of Germany .
7015998 6/1971 Netherlands .

*Primary Examiner*—Robert W. Ramsuer

[57] ABSTRACT

The invention provides furanone derivatives of the general formula

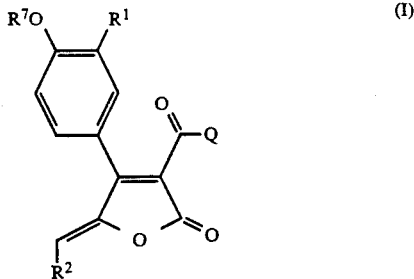

in which $R^1$ represents a halogen atom or an optionally substituted alkyl or alkoxy group, $R^2$ represents a halogen atom or an optionally substituted alkyl, aryl or heterocyclyl group, $R^7$ represents a $C_{1-4}$ alkyl group and Q represents an optionally substituted morpholino or amino group; processes for their preparation; compositions containing such compounds and their use as fungicides.

9 Claims, No Drawings

FUNGICIDAL FURANONE DERIVATIVES

The present invention relates to certain furanone derivatives, processes for their preparation, compositions containing such compounds and their use as fungicides for the control of phytopathogenic fungi.

In German patent application DE 2,032,058 compounds of the general formula A are disclosed,

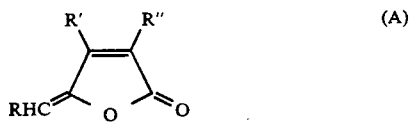

wherein R is hydrogen, phenyl, dimethyl amino, O-tolyl or 2,6-dichloro phenyl, R' is methyl or phenyl and R" is nitrile, p-nitro phenyl or carboxamide, as thermal stabilisers for poly(ethylene terephthalate). A similar furanone B

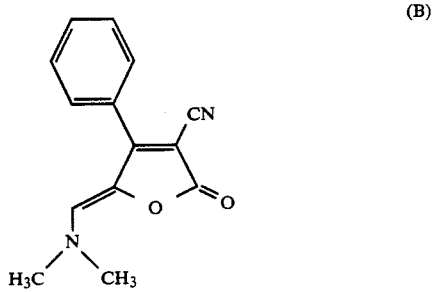

is disclosed in Dutch application NL 7015998 as herbicide and algicide.

It has been found now that certain new substituted furanones show an excellent fungicidal activity, particularly against *Phytophthora infestans* and *Plasmopara viticola*.

Accordingly, the present invention relates to compounds of the general formula I

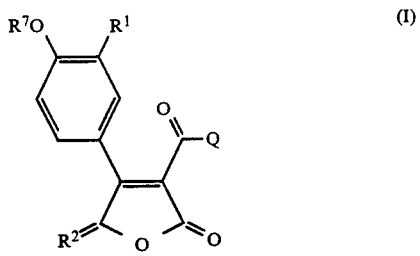

in which
$R^1$ represents a halogen atom or an optionally substituted alkyl or alkoxy group,
$R^2$ represents a halogen atom or an optionally substituted alkyl, aryl or heterocyclyl group, Q represents an optionally substituted morpholino or amino group, and
$R^7$ represents a $C_{1-4}$ alkyl group.

Alkyl as substituent or as part of other substituents, such as alkoxy, for example may contain up to 12, preferably up to 6, and especially up to 4, carbon atoms and includes the following straight-chain or branched groups depending on the number of carbon atoms indicated: methyl, ethyl, propyl, butyl, pentyl, hexyl, heptyl, octyl, etc. as well as their isomers such as isopropyl, isobutyl, tertiary-butyl, isopentyl. Halogen includes fluorine, chlorine, bromine or iodine, especially fluorine, chlorine and bromine. Cycloalkyl may contain 3 to 8, preferably 3 to 6, carbon atoms and includes the following substituents depending on the number of carbon atoms indicated: cyclopropyl, cyclobutyl, cyclopentyl, cyclohexyl, cycloheptyl etc. Generally, substituents of alkyl, alkenyl, alkynyl, cycloalkyl and phenyl preferably are halogen, methoxy, nitro, amino, cyano and, in the case of cycloalkyl and phenyl, also methyl and trifluoromethyl. Sulphanyl stands for the -S- moiety. 5- or 6-membered heterocycle preferably means a saturated or unsaturated 5- or 6-membered heterocycle containing one to four of the same or different heteroatoms such as nitrogen, oxygen or sulphur. Typical examples for such heterocycles are tetrahydrofuran, furan, tetrahydrothiophene, thiophene, pyrrolidine, pyrrole, pyrroline, pyrazole, imidazole, triazole, tetrazole, pyrazoline, oxazole, thiazole, isoxazole, isothiazole, pyran, dihydropyran, tetrahydropyran, thiopyran, dihydrothiopyran, tetrahydrothiopyran, pyridine, piperidine, pyridazine, dihydropyridazine, tetrahydropyridazine, pyrimidine, dihydropyrimidine, tetrahydropyrimidine, pyrazine, dihydropyrazine, tetrahydropyrazine, morpholine, thiazine, dihydrothiazine, tetrahydrothiazine, piperazine or triazine.

The compounds of the invention exhibit excellent fungicidal activity, particularly against *Phytophthora infestans* and *Plasmopara viticola*. Preferred compounds of formula I are those in which
$R^1$ is halogen, straight-chain or branched $C_1$-$C_6$-alkyl, optionally substituted by one or more of the same or different halogen atoms, straight-chain or branched $C_1$-$C_6$-alkoxy, optionally substituted by one or more of the same or different halogen atoms,
$R^2$ is a straight-chain or branched $C_1$-$C_6$-alkyl, optionally substituted by one or more of the same or different halogen atoms,

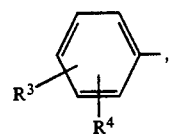

naphthyl
or a 5- or 6-membered heterocycle, optionally substituted by one or more of the same or different halogen atoms.
$R^3$ and $R^4$ are independently or simultaneously hydrogen, halogen, straight-chain or branched $C_1$-$C_6$-alkyl, optionally substituted by one or more of the same or different halogen atoms, straight-chain or branched $C_1$-$C_6$-alkoxy, optionally substituted by one or more of the same or different halogen atoms, nitro, dimethylamino, phenyl, optionally substituted phenoxy or optionally substituted phenylsulphanyl,
$R^7$ is methyl,
Q is optionally substituted morpholine or

$R^5$ is straight-chain or branched $C_1$–$C_6$-alkyl, optionally substituted by cycloalkyl, phenyl or cyano, or phenyl, and $R^6$ is methyl or ethyl, preferably methyl. Good results in terms of control of phytopathogenic fungi were obtained with compounds of general formula I $R^1$ is straight-chain or branched $C_1$–$C_6$-alkoxy, optionally substituted by one or more of the same or different halogen atoms.

$R^2$ is straight-chain or branched $C_1$–$C_6$-alkyl, optionally substituted by one or more of the same or different halogen atoms,

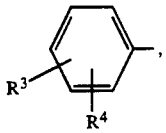

naphthyl, or a 5- or 6-membered heterocycle, optionally substituted by one or more of the same or different halogen atoms, $R^3$ and $R^4$ are independently or simultaneously hydrogen, halogen, straight-chain or branched $C_1$–$C_6$-alkyl, optionally substituted by one or more of the same or different halogen atoms, straight-chain or branched $C_1$–$C_6$-alkoxy, optionally substituted by one or more of the same or different halogen atoms, nitro, dimethyl- amino, phenyl, optionally substituted phenoxy or optionally substituted phenylsulphanyl, $R^7$ is methyl, and Q is optionally substituted morpholine. Especially good control of *Phytophthora infestans* and *Plasmopara viticola* was achieved by compounds of general formula I wherein $R^1$ is methoxy $R^2$ is straight-chain or branched $C_1$–$C_6$-alkyl, optionally substituted by one or more of the same or different halogen atoms,

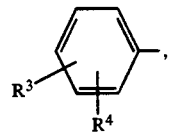

naphthyl, or a 5- or 6-membered heterocycle, optionally substituted by one or more chlorine atoms, $R^3$ and $R^4$ are independently or simultaneously hydrogen, halogen, straight-chain or branched $C_1$–$C_6$-alkyl, optionally substituted by one or more of the same or different halogen atoms, straight-chain or branched $C_1$–$C_6$-alkoxy, optionally substituted by one or more of the same or different halogen atoms, nitro, dimethyl amino or phenyl, $R^7$ is methyl, and Q is morpholine.

The present invention also provides a process for the preparation of a compound of general formula I wherein $R^1$ to R and Q are as hereinbefore defined by reacting a compound of general formula II

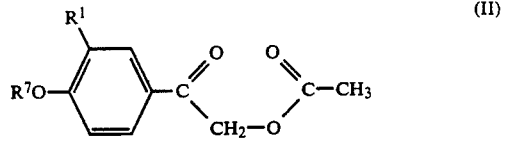

wherein $R^1$ and $R^7$ as hereinbefore defined with a compound of general formula III

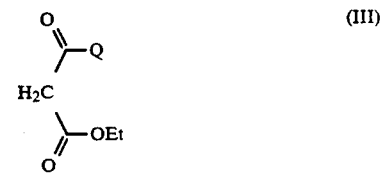

wherein

Q, and $R^5$ and $R^6$ are as hereinbefore defined and, subsequently, reacting the product of this first step with a compound of general formula IV

wherein $R^2$, $R^3$ and $R^4$ are as hereinbefore defined.

Preferably, the reaction is carried out as follows: An appropriately substituted α-acetoxy ketone of general formula II, which may have been prepared by known methods as described in e.g. A. Kaufmann and H. Müller, *Chem. Ber.* 51, 128 (1918) or D. D. Pratt and R. Robinson, *J. Chem. Soc.* 123, 756 (1923) is reacted with a malonic acid amide ester prepared e.g. according to M. Mazzei, G. Roma and A. Ermili, *Farmaco Ed. Sci.* 34, 52–61 (1979) in the presence of a base. The process is carried out in a way known in principle, whereby, if practicable, inert solvents which do not interfere with the reaction or mixtures of such solvents are used, e.g. methanol, ethanol toluene, benzene, xylene, diglyme, diethyl ether, tetrahydrofurane. According to the reactivity of the components the reaction is carried out with cooling, at room temperature or at elevated temperature up to the boiling point of the reaction mixture. Generally, the reaction takes places at temperatures in the range of −10° C. to ambient temperature, preferably, under chilling with ice. The base may be any base such as alkali metal carbonates, alkali metal hydroxides, alcoholates or hydrides, however, generally, it is advantageous to employ a strong base such as alkali metal hydroxides or alkali metal alcoholates. After neutralization of the reaction mixture, the isolation of the product may be carried out according to prior art. The product is then reacted with an aldehyde of general formula IV in the presence of a base. The reaction is carried out in an inert solvent e.g. methanol, ethanol, ether, tetrahydrofurane, 1,4-dioxane, toluene, etc, or mixtures thereof at a temperature in the range from ambient temperature to the boiling point of the reaction mixture. Generally, the reaction is carried out under heating of the mixture to reflux. The base may be any Lewis base, however, in practice, secondary and tertiary amines are very suitable. The isolation of the product may be carried out by techniques known from prior art.

The compounds according to formula I possess fungicidal properties which are superior to those known from prior art, especially in respect to selectivity and spectrum of activity.

The invention also provides fungicidal compositions which comprise at least one of the compounds according to general formula I as well as procedures for control of phytopahtogenic fungi.

The compounds according to general formula I may be used as such, however, they are preferably used as compositions comprising besides the compounds according to the invention adjuvants and auxiliaries which are known for formulation purposes and are manufactured into e.g. emulsion concentrates, solutions which may be sprayed directly or diluted, diluted emulsions, wettable powders, soluble powders, dusts, granulates, microencapsulates by well-established procedures. The form of application such as spraying, atomizing, dispersing, pouring may be chosen like the compositions according to the desired objectives and the given circumstances.

The formulations, i.e. the compositions which comprise at least one compound according to general formula I and optionally solid and/or liquid auxiliaries and adjuvants, may be prepared by well-established procedures, e.g. intensive mixing and/or grinding of the active ingredients with other substances, such as fillers, solvents, solid carriers, and optionally surface-active compounds (tensides).

Solvents may be aromatic hydrocarbons, preferably the fractions $C_8$ to $C_{12}$, e.g. xylenes or xylene mixtures, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl 2-pyrrolidone, dimethyl sulfoxide, alkyl formamides, epoxidized vegetable oils, e.g. epoxidized coconut or soybean oil, water.

Solid carriers, which may be used for dusts or dispergible powders, may be mineral fillers, such as calcite, talc, kaolin, montmorillonite, attapulgite. The physical properties may be improved by addition of highly dispersed silica gel or highly dispersed polymers. Carriers for granulates may be porous material, e.g. pumice, broken brick, sepiolite, bentonite, non-sorptive carriers may be calcite or sand. Additionally, a multitude of pre-granulated inorganic or organic materials may be used, such as dolomite or crushed plant residues.

Suitable surface-active substances may be non-ionogenic, anionic or cationic tensides with good dispersing, emulgating and wetting properties depending on the nature of the compound according to general formula I to be formulated. Tensides may also mean mixtures of tensides.

Suitable tensides may be so-called water-soluble soaps as well as water-soluble synthetic surface-active compounds.

Soaps usually are alkali, earth alkali or optionally substituted ammonium salts of higher fatty acids ($C_{10}$–$C_{20}$), e.g. the sodium or potassium salts of oleic or stearic acid or of mixtures of natural fatty acids which are prepared, for example, from coconut or tallow oil. Furthermore, methyl-taurin salts of fatty acids may be used.

However, so-called synthetic tensides are preferably used, especially fatty sulphonates, fatty sulphates, sulphonated benzimidazole derivatives or alkyl aryl sulphonates.

The fatty sulphates or fatty sulphonates are normally used as alkali, earth alkali or optionally substituted ammonium salts and have an alkyl moiety of 8 to 22 carbon atoms, whereby alkyl also means the alkyl moiety of acyl residues, such as the sodium or calcium salt of lignin sulphonic acid, of sulphuric acid dodecylate or of a mixture of fatty alcohols prepared from natural fatty acids. This also includes the salts of sulphuric acid esters, sulphonic acids and adducts of fatty alcohols and ethylene oxide. The sulphonated benzimidazole derivatives preferably contain 2 sulphonic acid residues and a fatty acid residue with 8 to 22 carbon atoms. Alkyl aryl sulphonates are, for example, the sodium, calcium or triethyl ammonium salts of dodecyl benzene sulphonic acid, dibutyl naphthalene sulphonic acid or of a condensate of naphthalene sulphonic acid and formaldehyde.

Furthermore, phosphates, such as the salts of the phosphoric acid ester of a p-nonylphenol-(4-14)-ethylene oxide adduct or phospholipids, may be used.

Non-ionic tensides are preferably polyglycolether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols.

Other suitable non-ionic tensides are the water-soluble, 20 to 250 ethylene glycol ether groups containing polyadducts of ethylene oxide and polypropylene glycol, ethylene diamino polypropylene glycol and alkyl polypropylene glycol with 1 to 10 carbon atoms in the alkyl moiety, the substances normally contain 1 to 5 ethylene glycol units per propylene glycol unit.

Examples of non-ionic tensides are nonylphenol polyethoxy ethanols, castor oil polyglycol ether, polyadducts of ethylene oxide and polypropylene, tributyl phenoxy polyethoxy ethanol, polyethylene glycol, octyl phenoxy polyethoxy ethanol.

Furthermore, fatty acid esters of polyoxy ethylene sorbitan, such as polyoxy ethylene sorbitan trioleate may be used.

Cationic tensides preferably are quaternary ammonium salts, which have at least one alkyl residue with 8 to 22 carbon atoms and, furthermore, low, optionally-halogenated alkyl, benzyl or hydroxyalkyl residues. The salts are preferably halides, methyl sulphates or alkyl sulphates, e.g. stearyl trimethyl ammonium chloride or benzyl bis(2-chloroethyl) ethyl ammonium bromide.

The tensides generally used for compositions are disclosed in publications as:

"McCutheon's Detergents and Emulsifiers Annual", MC Publishing Corp., Ridgewood, NJ, USA 1981;

H. Stache, "Tensid-Taschenbuch", 2nd ed., C. Hanser, Munich, Vienna, 1981;

M. and J. Ash, "Encyclopedia of Surfactants", vol. I–III, Chemical Publishing Co., New York, NY, USA 1980–1981.

The pesticidal compositions usually comprise 0.1% to 95%, preferably 0.1% to 80% of at least one compound according to general formula I, 1% to 99.9% of a solid or liquid adjuvant and 0% to 25%, preferably 0.1% to 25%, of a tenside.

The preferred compositions usually comprise:

| Emulsion Concentrates: | | | | |
|---|---|---|---|---|
| Active ingredient: | 1% to 20%, | preferably | 5% to 10% | |
| Surface-active substance: | 5% to 30%, | preferably | 10% to 20% | |
| Liquid carrier: | 50% to 94%, | perferably | 70% to 85% | |
| Suspension-Concentrates: | | | | |
| Active ingredient: | 5% to 75%, | preferably | 10% to 50% | |
| Water: | 94% to 24%, | preferably | 88% to 30% | |
| Surface-active substance: | 1% to 40%, | preferably | 2% to 30% | |
| Wettable Powder: | | | | |
| Active ingredient: | 0.5% to 90%, | preferably | 1% to 80% | |
| Surface-active substance: | 0.5% to 20%, | preferably | 1% to 15% | |
| Solid carrier: | 5% to 95%, | preferably | 15% to 90% | |
| Dusts: | | | | |
| Active ingredient: | 0.1% to 10%, | preferably | 0.1% to 1% | |
| Solid carrier: | 99.9% to 90%, | preferably | 99.9% to 99% | |
| Granulates: | | | | |
| Active ingredient: | 0.5% to 30%, | preferably | 3% to 15% | |
| Solid carrier: | 99.5% to 70%, | preferably | 97% to 85% | |

As commodity the compositions may preferably be in a concentrated form whereas the end-user generally employs diluted compositions. The compositions may be diluted to a concentration of 0.001% of active ingredient (a.i.). The doses usually are in the range from 0.01 to 10 kg a.i./ha.

The compositions may also comprise other auxiliaries such as stabilizers, defoamer, viscosity controlling agents, thickeners, adhesives, fertilisers or other active ingredients to obtain special effects.

The following examples further illustrate the invention without limiting them to the compounds, compositions or methods described therein.

EXAMPLES

EXAMPLE 1

5-(4-Chlorobenzylidene)-4-(3,4-dimethoxyphenyl)-2-oxo-2,5-dihydrofurane-3-carboxylic acid morpholide a) Malonic acid ethylester morpholide Morpholine (87.0 g, 1.0 mol) was added to malonic acid diethyl ester (160.0 g, 1.0 mol) within 4 h under stirring at 150° C. The temperature dropped to 110° C. because of generated, refluxing ethanol. The reaction mixture was stirred for another 16 h under reflux, then the ethanol was evaporated and the residue fractionated in vacuo.

Yield: 90.3 g (45% of theoretical)
Bp.$_{0.05\ mbar}$: 123° C.
Mp.: 63°–64° C.

b) 2-Acetoxy-3',4'-dimethoxy acetophenone:

Sodium acetate (10.70 g, 130 mmol) and 2-bromo-3',4'-dimethoxy acetophenone (25.90 g, 100 mmol) were successively added to a stirred mixture of glacial acetic acid (40 ml) and acetanhydride 4 ml) at 90° C. The reaction mixture was stirred for 2 h at 125° C., then excessive acetic acid and acetanhydride were evaporated. The residue was extracted at 50° C. with a mixture of toluene (160 ml) and water (160 ml), the organic layer then washed with warm water and dried. The crystallisation which started upon cooling down of the solution was completed by careful addition of petrol ether. The crystals of 2-acetoxy-3',4'-dimethoxy acetophenone were recovered, washed with toluene/petrol ether (1:3) and dried.

Yield: 20.25 g (85% of th.)
Mp.: 85° C.

c) 4-(3,4-Dimethoxyphenyl)-2-oxo-2,5-dihydrofurane-3-carboxylic acid morpholide

2-Acetoxy-3',4'-dimethoxy acetophenone (23.8 g, 100 mmol) and malonic acid ethylester morpholide (20.1 g, 100 mmol) were stirred in methanol (60 ml) in an ice bath. A solution of potassium hydroxide (5.6 g, 100 mmol) in methanol (40 ml) was added within 30 min, the resulting solution was stirred another 30 min at 10° C. Subsequently, the reaction mixture was stirred into a solution of concentrated hydrochloric acid (40 ml) in ice water (800 ml). The yellow solution thereupon obtained was extracted five times with chloroform (30 ml each), the organic layer was dried and the solvent evaporated. The red residue was dissolved in warm acetone (20 ml), the solution was added to toluene (180 ml) and applied onto a flash-chromatography column (silica gel, 350 g). The column was eluted with toluene/acetone mixtures (9:1, 1 l; 8:2, 0.5 l; 7:3, 1 l). The fractions containing 4-(3,4-dimethoxyphenyl)-2-oxo-2,5-dihydrofurane-3-carboxylic acid morpholide, which strongly fluoresces light-blue in UV-light, were collected and the solven was evaporated whereupon the compound crystalised. The material was collected by vacuum filtration, washed with toluene and dried.

Yield: 15.2 g (46% of th.)
R$_f$(toluene/acetone, 2:3): 0.56
Mp.: 167° C.

d) 5-(4-Chlorobenzylidene)-4-(3,4-dimethoxyphenyl)-2-oxo-2,5-dihydro-furane-3-carboxylic acid morpholide:

4-(3,4-Dimethoxyphenyl)-2-oxo-2,5-dihydrofurane-3-carboxylic acid morpholide (1.00 g, 3 mmol) and 4-chlorobenzaldehyde (0.42 g, 3 mmol) were refluxed with ethanol (15 ml) and a small amount of piperidine (3 drops) for 3 h, then the reaction mixture was concentrated. The residue was dissolved in ethyl acetate (5 ml), petrol ether (2.5 ml) was added and the solution was applied onto a flash chromatography column (silica gel, 30 g). The column was eluted with ethyl acetate/petrol ether (2:1). The fractions containing the compound with the R$_f$(ethyl acetate/petrol ether, 2:1): 0.32 were collected and concentrated. 5-(4-Chlorobenzylidene)-4-(3,4-dimethoxyphenyl)-2-oxo-2,5-dihydro-furane-3-carboxylic acid morpholide was precipitated by addition of petrol ether.

Yield: 0.90 g (66% of th.)
Mp.: 191° C.

The following examples were prepared analogously with the exception that readily crystallising compounds were not chromatographed.

TABLE 1
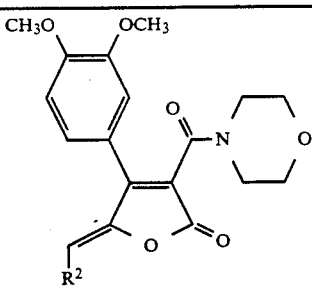
| No. | R² | Mp. [°C.] | R_f (toluene/acetone, 7:3) |
|---|---|---|---|
| 2 | 2-Cl-C₆H₄- | 214 | 0.61 |
| 3 | 3-Cl-C₆H₄- | 168 | 0.55 |
| 4 | 4-CH₃-C₆H₄- | 168 | 0.56 |
| 5 | C₆H₅- | 164 | 0.52 |
| 6 | 3-CH₃O-C₆H₄- | 126 | 0.54 |
| 7 | 4-biphenyl- | 178 | 0.56 |
| 8 | 4-O₂N-C₆H₄- | 198 | 0.58 |
| 9 | 4-(H₃C)₂N-C₆H₄- | 128 (decomp.) | 0.50 |
| 10 | 2,4-Cl₂-C₆H₃- | 220 | — |
| 11 | 2-naphthyl- | 222 | 0.60 |
TABLE 1-continued
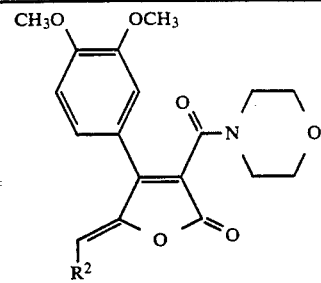
| No. | R² | Mp. [°C.] | R_f (toluene/acetone, 7:3) |
|---|---|---|---|
| 12 | 2-thienyl- | 172 | 0.54 |
| 13 | 3-pyridyl- | 194 | 0.24 |
| 14 | 2-pyridyl- | 168 | 0.43 |
| 15 | 4-(H₃C)₃C-C₆H₄- | oil | 0.60 |
| 16 | 4-Br-C₆H₄- | 192 | 0.57 |
| 17 | 4-CF₃-C₆H₄- | 85–90 | 0.57 |
| 18 | 2-furyl- | 121 | 0.52 |
| 19 | 5-Cl-2-thienyl- | 210 | 0.50 |
| 20 | 3,5-Cl₂-C₆H₃- | 170 | — |
EXAMPLE 20:
Biological Testing
a) *Phytophthora infestans* in tomatoes:

After the development of the cotyledons, tomato plants (cv Prof. Rudloff) were transferred into 6-cm plastic pots containing Frustosoil ® N as substrate. The plants were kept in a greenhouse at a temperature of 23° C. during day-time and 18° C. at night. The relative humidity was between 50% and 70%. When the first leaves had developed the plants were ready for fungicide application.

4–6 Plants per treatment were used. The application of the fungicides was carried out 5 days before infection. The test plants were sprayed to run-off in a spray cabinet using 20 ml of spraywash. Then the plants were again kept in the greenhouse under the conditions described in the previous paragraph.

The plants were artificially infected with an aqueous spore suspension of *Phytophthora infestans* containing 300,000 spores/ml. Infection was accomplished by spraying the upper side of the leaves with the spore suspension. Then the plants were immediately incubated at 100% humidity for 48 h in the dark. Symptoms developed rapidly when the plants were transferred into the greenhouse with low relative humidity (approx. 50%).

Evaluation (table 2) was carried out by estimating the percentage of diseased leaf area and the following scale was used:

1 = less than 10% of infection
2 = between 11% and 40% of infection
3 = more than 41% of infection.

b) *Plasmopara viticola* in vines

Cuttings of the cultivar Müller-Thurgau were grown in the greenhouse at 25° C. and 50–70% relative humidity. When 6–8 leaves had developed, the plants were cut back to 3–4 equally sized leaves. The plants were further cultivated in plastic pots ($\phi$12 cm).

The plants were artificially infected with an aqueous spore suspension of *Plasmopara viticola* containing 200,000 spores/ml. Infection was accomplished by spraying the lower side of the leaves with the spore suspension. Then the plants were immediately incubated at 100% relative humidity for 48 h.

Four to six plants per treatment were used for the application of the test compounds. The application was carried out 48 h after infection. The test plants were sprayed to run off in a spray cabinet using 20 ml of spray wash. Then the plants were kept at high humidity in the greenhouse at 23° C. during day-time and 18° C. at night until symptoms developed.

Evaluation was carried out as described above. The results are compiled in table 2.

TABLE 2

| No. | P. infestans | P. viticola |
|---|---|---|
| table 1, no. 2 | 1 | 1 |
| table 1, no. 3 | 1 | 1 |
| table 1, no. 4 | 2 | 1 |
| table 1, no. 5 | 1 | 1 |
| table 1, no. 6 | 1 | 1 |
| table 1, no. 7 | 1 | 1 |
| table 1, no. 8 | 1 | 1 |
| table 1, no. 9 | 1 | 1 |
| table 1, no. 10 | 1 | 2 |
| table 1, no. 11 | 1 | 1 |
| table 1, no. 12 | 1 | 1 |

TABLE 2-continued

| No. | P. infestans | P. viticola |
|---|---|---|
| table 1, no. 13 | 1 | 1 |
| table 1, no. 14 | 1 | 1 | c) *Plasmopara viticola* in vines

Single-bud Müller-Thurgau cuttings are cultivated in a hothouse at 25° C. and 50–70% RH. Once the plants have formed 6–8 leaves they are cut back to three equal-sized leaves. Frusto soil is used as substrate.

A spore suspension for artificial infection is prepared by shaking sporulating vine leaves which had been infected with *Plasmopora viticola* one week previously with distilled water in a graduated flask until sufficient sporangia have been shaken off the leaves. Then the water is filtered through a sieve and the suspension of sporangia set at 500,000/ml.

An acetone spray liquid master solution containing 5000 ppm a.s. and 5000 ppm Triton X is prepared, and diluted to the desired concentration.

Two vine plants are placed in a closed spray cabin and sprayed to run-off using 3 nozzles. The spray liquid requirement is 20 ml. The concentrations used are 100 and 25 ppm.

Twenty four hours after the application the test plants are infected by spraying with a suspension of *Plasmopara viticola* sporangia. After a 48 hour incubation period in a dark, damp chamber the plants are placed in a hothouse cabinet at 100% RH and 23° C.

The percentage sporulating leaf underside Table 3 is evaluated after 7 days according to the scale:

1 = 0–10% infection
2 = 11–40% infection
3 = 41–100% infection

TABLE 3

| | P. viticola | |
|---|---|---|
| No. | (100 ppm) | (25 ppm) |
| Table, no. 8 | 1 | 2 |
| Table, no. 9 | 1 | 2 | d) Determination of minimal inhibition concentration (MIC value) against *Phythophtora infestans*

Ten test tubes (16×160 mm, with aluminum cap, Schott, Mainz, FRG) per compound were filled with nutrient solution (V8-juice, 3 ml) and autoclaved. After cooling down, sterile nutrient solution (3 ml) containing the active compound (200 µg/ml) was pipetted into the first tube and mixed. Then, half the content of the first tube (3 ml) was transferred to the second tube, mixed and, again, half the content of this tube transferred to the third and so on. By this means, the following series of test solutions was prepared:

| Tube No. | 1 | 2 | 3 | 4 | 5 | 6 | 7 | 8 | 9 | 10 |
|---|---|---|---|---|---|---|---|---|---|---|
| Concentration (a.i. µg/ml) | 100 | 50 | 25 | 12.5 | 6.25 | 3.13 | 1.56 | 0.78 | 0.39 | 0.2 |

The tubes were inoculated with a sporangia suspension (0.1 ml < spore density $10^6$/ml) of *Phythophthora infestans* (laboratory strain). After an incubation time of 7 days at 18° C., the assessment was carried out by visual inspection of the test tubes. The lowest concentration in the test tubes without mycelium growth was recorded as minimal inhibition concentration (table 4). All experiments were carried together with a reference compound (3-(4-chlorophenyl-3-(3,4-dimethoxyphenyl)acrylic acid morpholide).

TABLE 4

| Compound | M.I.C. value | Reference compound |
| --- | --- | --- |
| Example 1 | 0.78 | (0.78) |
| Table, no. 15 | 0.78 | (1.56) |
| Table, no. 16 | 1.56 | (1.56) |
| Table, no. 17 | 3.13 | (1.56) |
| Table, no. 18 | 25 | (1.56) |
| Table, no. 19 | 3.13 | (1.56) |
| Table, no. 20 | 6.25 | (0.39) | e) Direct protectant activity against vine downy mildew (*Plasmopara viticola*)

The test is a direct protectant one using a foliar spray. The lower surface of leaves of whole vine plants (cv Cabernet Sauvignon) are sprayed with the test compound at a dosage of 1000 ppm using an automated sprayline with an atomising nozzle, and after a subsequent period of 24 hours under normal glasshouse conditions the lower surfaces of the leaves are inoculated by spraying with an aqueous suspension containing $2.5 \times 10^4$ zoosporangia/ml. The inoculated plants are kept for 24 hours in a high humidity cabinet, 5 days under normal glasshouse condition and then returned for a further 24 hours to high humidity. Assessment (Table 5) is based on the percentage of leaf area covered by sporulation compared with that on control leaves according to criteria:

0 = less than 50% disease control
1 = about 50–80 disease control
2 = greater than 80% disease control

TABLE 5

| Compound | |
| --- | --- |
| Table, no. 18 | 2 |
| Table, no. 19 | 2 | f) Direct protectant activity against vine downy mildew (*Plasmopora viticola*).

The test described under e was repeated, using different concentrations. The assessment (Table 6) was done on a scale from 0 to 9, 9 being 100% control.

TABLE 6

| Compound | 300 ppm | 100 ppm |
| --- | --- | --- |
| Table, no. 16 | 4.0 | 4.7 |
| Table, no. 17 | 6.0 | 5.3 |

We claim:

1. A compound of the formula

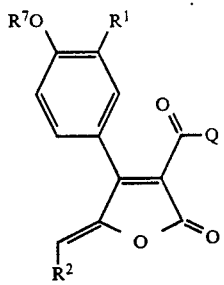

(I)

in which
R[1] represents a halogen atom or an optionally substituted alkyl or alkoxy group,
R[2] represents a halogen atom or an optionally substituted alkyl, aryl or heterocyclyl group,
R[7] represents a $C_{1-4}$ alkyl group, and
Q represents an optionally substituted morpholino or amino group.

2. A compound according to claim 1 in which R[1] represents a halogen atom or a $C_{1-6}$ alkyl or $C_{1-6}$ alkoxy group optionally substituted by one or more halogen atoms.

3. A compound according to claim 1 in which R[2] represents a halogen atom, a $C_{1-6}$ alkyl, naphthyl or 5- or 6-membered heterocyclyl group each optionally substituted by one or more halogen atoms, or a group

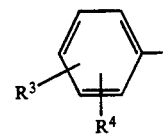

where R[3] and R[4] independently represent a hydrogen or halogen atom or a $C_{1-6}$ alkyl, $C_{1-6}$ haloalkyl, $C_{1-6}$ alkoxy, $C_{1-6}$ haloalkoxy, nitro, amino, $C_{1-6}$ alkylmino, di-$C_{1-6}$ alkylamino or phenyl group.

4. A compound according to claim 1 in which Q represents a morpholino group or a group

where R[5] represents a phenyl group or a $C_{1-6}$ alkyl group optionally substituted by a $C_{3-8}$ cycloalkyl, phenyl or cyano group, and R[6] represents methyl or ethyl.

5. A compound according to claim 1 in which R[1] represents a methoxy group; R[2] represents a naphthyl, pyridyl, furyl, thienyl, chlorothienyl, phenyl, chlorophenyl, dichlorophenyl, methylphenyl, bromophenyl, butylphenyl, methoxyphenyl, nitrophenyl, trifluoromethyl phenyl, dimethylaminophenyl or biphenyl group; R[7] represents methyl and Q represents a morpholino group.

6. A fungicidal composition which comprises a carrier and, as active ingredient, a compound of formula I as defined in claim 1.

7. A method of combating fungus at a locus which comprises treating the locus with a fungicidally effective amount of a compound of formula I as defined in claim 1.

8. A method according to claim 7 in which the locus comprises plants subject to or subjected to fungal attack, seeds of such plants or the medium in which the plants are growing or are to be grown.

9. A method of combating fungus at a locus which comprises treating the locus with a fungicidally effective amount of a composition as defined in claim 6.

* * * * *